United States Patent [19]

Sakuma

[11] Patent Number: 5,456,602
[45] Date of Patent: Oct. 10, 1995

[54] DENTAL BONDING

[75] Inventor: Tetsuro Sakuma, Tokorozawa, Japan

[73] Assignee: GC Corporation, Tokyo, Japan

[21] Appl. No.: 184,936

[22] Filed: Jan. 24, 1994

[30] Foreign Application Priority Data

Jan. 29, 1993 [JP] Japan .................................. 5-032542

[51] Int. Cl.⁶ .................................................. A61C 5/00
[52] U.S. Cl. ........................... 433/215; 433/228.1; 106/35
[58] Field of Search ................................. 433/9, 24, 215, 433/216, 228.1; 106/35

[56] References Cited

U.S. PATENT DOCUMENTS

| | | | |
|---|---|---|---|
| 4,588,756 | 5/1986 | Bowen | 433/228.1 |
| 4,645,456 | 2/1987 | James | 433/228.1 |
| 4,952,613 | 8/1990 | Hosoda | 433/228.1 |
| 5,141,436 | 8/1992 | Orlowski et al. | 433/228.1 |
| 5,290,172 | 3/1994 | Sakuma et al. | 433/215 |

*Primary Examiner*—Cary E. O'Connor
*Attorney, Agent, or Firm*—Oblon, Spivak, McClelland, Maier & Neustadt

[57] ABSTRACT

A dental bonding method comprises the steps of treating enamel and dentine with a tooth surface-treating material containing organic acid, iron or copper salt, and water, followed by water washing and drying; applying on the thus treated surface a primer containing organic acid, water, and hydrophilic methacrylate, followed by drying; and applying on the thus coated surface a dental bonding material containing methacrylate or acrylate having at least one unsaturated double bond, and polymerization initiator optionally with carbodiimide compound, for surface curing.

11 Claims, No Drawings

1

DENTAL BONDING

BACKGROUND OF THE INVENTION

The present invention relates generally to a dental method of bonding acrylic resin to teeth, and more particularly to a dental method of bonding dental composite resin to teeth for restoring them.

So far, restoring composite resin has been bonded to enamel by etching the enamel with phosphoric or citric acid, washing the enamel with water, followed by drying. Treating the enamel even with a bonding material which is composed of a methacrylate ester monomer and a curing agent and has no adhesion to dentine. With this bonding material, a clinically sufficient bonding strength more than 100 kg/cm$^2$ is obtained between the restoring composite resin and the enamel.

However, no sufficient adhesion is obtained to dentine with the use of a bonding material having no adhesion to the dentine. For instance, Japanese Patent Publication No. 56-33363 and Japanese Patent Publication No. 59-15468 propose to use initiators based on benzoyl peroxide-aromatic tertiary amine-sulfinic acid salt. Even with these initiators, however, no sufficient bonding strength is obtained with respect to the dentine. Various dentine-treating solutions or primers which have been said to have adhesion have also been put forward. For instance, Japanese Patent Publication No. 55-30768 discloses a phosphoric acid ester compound as having adhesion. As measured by the inventors, however, this ester is found to have no such high bonding strength. Also, Japanese Patent Application Laid-Open No. 61-183203, Japanese Patent Application Laid-Open No. 62-2321652, Japanese Patent Application Laid-Open No. 64-90108 and Japanese Patent Application Laid-Open No. 1-279815 disclose surface treating materials which appear to be similar to that disclosed in the present disclosure. However, nowhere in these specifications is described the bonding method envisaged in the present invention, and the inventions disclosed therein is quite different from the present invention in terms of what is intended. The bonding strength measured by the inventors are inferior to that achieved by the present invention.

In Japanese Patent Application Laid-Open No. 54-12338, 4-methacryloxyethyltrimellitic anhydride (hereinafter 4META for short) is disclosed as a functional monomer. Dentine is treated with an aqueous solution of 10% citric acid and 3% ferric chloride and then with a restoring filling material (4META-containing methyl methacrylate/tri-n-butylborane/polymethyl methacrylate), whereby a bonding strength of 12 to 18 MPa is achieved, as set forth in The "Journal of the Japan Society for Dental Apparatus and Materials", 23(61), 29–32, 1982. However, such high strength could not be obtained by the bonding method of the inventors of the present invention. As set forth in The "Journal of the Japan Research Society of Dental Materials and Appliances", Vol. 8 (an extra issue No. 14), pp. 89–90 (1989) and Japanese Patent Application Laid-Open No. 4-126703, on the other hand, it has now been found that initiators based on (thio)barbituric acid derivative/copper compound/chlorine ions are considerably effective for achieving bonding strength with respect to the dentine.

However, the mixed powder/liquid curing type much the same as tri-n-butylborane involves troublesome problems in handling in pre-treating tooth surfaces. Such type is not always sufficient in bonding strength obtained. Thus, there is left much to be improved. Moreover, Japanese Patent Application Laid-Open No. 55-164611 discloses a dental resin composition comprising a carbodiimide compound and an acidic monomer, but this composition has a bonding strength as low as several tens kg/cm$^2$ and, in this respect, is inferior to currently available dental adhesives.

In view of the present situation where any clinically satisfactory bonding material is not obtained in terms of adhesion to the dentine, the inventors have made studies of how to improve adhesion to the dentine and consequently accomplished the present invention.

According to the present invention accomplished as a result of intensive studies made so as to solve the present problems mentioned above, a bonding method different from the conventional methods in terms of conception has been discovered.

More specifically, a smear layer that is "scum" resulting from the cutting of the teeth is removed by an organic acid incorporated in a treating material and, at the same time, collagenic denaturization of the surfaces of the teeth is inhibited by an iron or copper salt incorporated in the treating material. Then, a primer is applied to the teeth so as to allow a hydrophilic monomer and the organic acid to penetrate deep into the teeth, so that the organic acid can have a chelate bond with respect to calcium that is an inorganic component of the teeth. In addition, the hydrophilic monomer (a methacrylate having a hydroxyl group) bonds to the carboxylic acid and amino group of the activated collagen by way of hydrogen bonds, and this appears to be the reason for the hydrophilic monomer bonding strongly to the dentine. If a carbodiimide compound is additionally incorporated in the bonding material, it is possible to make a strong bond between collagen and the monomer through the dehydrating catalysis of the carbodiimide compound.

This carbodiimide compound is also expected to make a well durable bonding strength, because it causes the carboxylic acid and amino groups in collagen to be bonded together for collagenous crosslinking. In addition, this compound acts similarly on the carboxylic acid residue of the organic acid that is the previously applied primer component. These are considered to cooperate together to allow the bonding material to be bonded to both the inorganic and organic components of the dentine and the bonding chains to be bonded together, thereby achieving a significant improvement in the adhesion strength to the dentine.

SUMMARY OF THE INVENTION

According to one aspect of the invention, there is provided a dental bonding method comprising the steps of treating the enamel and dentine with a tooth surface-treating material containing (a) an organic acid, (b) an iron or copper salt, and (c) water, followed by water washing and drying; applying on the thus treated surface a primer containing (a) an organic acid, (c) water, and (d) a hydrophilic methacrylate, followed by drying; and applying on the thus coated surface a dental bonding material containing (e) a methacrylate or acrylate having at least one unsaturated double bond, (f) a polymerization initiator, and (g) carbodiimide compound for surface curing.

In particular, the four essential components (a) organic acid of the surface-treating material, (a) organic acid of the primer, (b) iron or copper salt, (d) hydrophilic methacrylate or five essential components added to these by (g) carbodiimide compounds have shown high adhesion strength to the enamel and dentine, thus a dental bonding method superior in the peripheral sealability has been found.

Each component will be explained in detail.

Preferalby, the organic acid (a) is citric acid, succinic acid, oxalic acid, fumaric acid, tartaric acid, malic acid, maleic acid, ethylenediaminetetraacetic acid, polyacrylic acid, an acrylic acid-maleic acid copolymer, or a copolymer of acrylic acid with an organic acid having an unsaturated double bond.

Preferably, the concentration of the organic acid (a) in the tooth surface-treating material is 1 to 50% by weight on the basis of the total weight of the tooth surface-treating material. Preferably, the concentration of the organic acide (a) in the primer is 0.1–30% by weight on the basis of the total weight of the primer. Curability of the bonding material applied later becomes lower if the concentration is too high.

Preferably, the iron or copper salt (b) is ferric chloride, cupric chloride or acetylacetone copper.

Preferably, the concentration of the iron or copper salt (b) is 0.0005 to 50% by weight on the basis of the total weight of the tooth surface-treating material.

Preferably, the hydrophilic methacrylate (d) is 2-hydroxethyl methacrylate.

Preferably, the concentration of the hydrophilic methacrylate (d) is 1 to 90% by weight on the basis of the total weight of the primer.

Preferably, the concentration of the organic acid (a) is 0.1 to 30% by weight on the basis of the total weight of the primer.

Preferably, the carbodiimide compound (g) is 1-ethyl-3-(3-dimethylaminopropyl)carbodiimide.

Preferably, the concentration of the carbodiimide compound (g) is 0.1 to 10% by weight on the basis of the total weight of the dental bonding material.

DETAILED DESCRIPTION OF THE INVENTION

In what follows, each component will be explained at great length.

(a) The organic acid may be citric acid, succinic acid, oxalic acid, fumaric acid, tartaric acid, malic acid, maleic acid, ethylenediaminetetraacetic acid, polyacrlyic acid, an acrylic acid-maleic acid copolymer, and a copolymer of acrylic acid with an organic acid having an unsaturated double bond. The organic acid, when used in the form of the tooth surface-treating material, should preferably be used at a concentration of 1–50% by weight on the basis of the total weight of the treating material. The organic acid, when used in the form of the primer, should preferably be used at a concentration of 0.1 to 30% by weight on the basis of the total weight of the primer. If too much is used, the curing characteristics of the bonding material to be later applied will get worse.

(b) The iron or copper salt may be ferric chloride, ferrous chloride, ferric nitrate, ferric acetate, cupric chloride, cuprous chloride, cupric nitrate, cupric acetate, and acetylacetone copper. Preferably, these salts are used at a concentration of 0.0005 to 50% by weight on the basis of the total weight of the tooth surface-treating material.

(d) The hydrophilic methacrylate may be 2-hydroxy-ethyl methacrylate, 3-hydroxypropyl methacrylate, 2,3-dihydroxypropyl methacrylate, 2-hydroxy-1,3-dimethacryloxy-propane, or 2,2-bis[4-(2-hydroxy-3-methacryloxypropoxy) phenyl]. Of these, preference is given to 2-hydroxyethyl methacrylate. This methacrylate is preferably used at a concentration of 1 to 99% by weight on the basis of the total weight of the primer.

(e) The methacrylate or acrylate having at least one unsaturated double bond may illustratively be methyl methacrylate, ethyl methacrylate, isopropyl methacrylate, 2-hydroxyethyl methacrylate, 3-hydroxypropyl methacrylate, 2-hydroxy- 1,3-dimethacryloxypropane, n-butyl methacrylate, isobutyl methacrylate, tetrahydrofurfuryl methacrylate, glycidyl methacrylate, 2-methoxyethyl methacrylate, 2-ethylhexyl methacrylate, benzyl methacrylate, 2,2-bis (methacryloxyphenyl) propane, 2,2-bis[4-(2-hydroxy-3-methacryloxypropoxy) phenyl] propane, 2,2-bis(4-methacryloxy-diethoxyphenyl) propane, 2,2-bis(4-methacryloxypolyethoxyphenyl) propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentraerythritol trimethacrylate, trimethylolmethane trimethacrylate and penterythritol tetramethacrylate, or analogous acrylates as well as methacrylates and acrylates, each having an urethane bond in its molecule. Particular preference is given to di-2-methacryloxyethyl- 2,2,4-trimethylhexamethylene dicarbamate or acrylate, and a methacrylate or acrylate having the following structural formula:

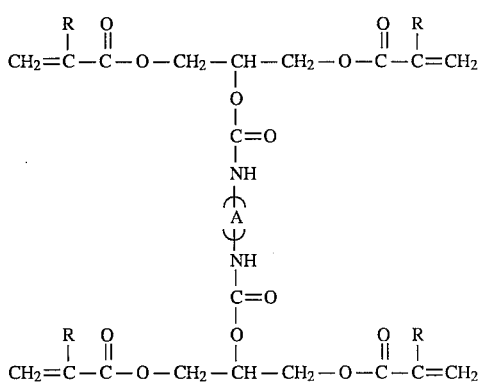

In which, R is H or CH$_2$ of the same or different kind, and
—(A)— denotes
—(CH$_2$)$_6$—,

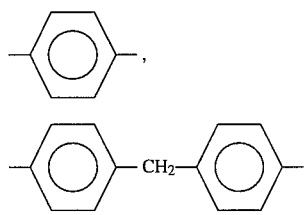

These methacrylates and acrylates are preferred and well-known dental materials, and may be used alone or in admixture, if required.

(f) In recent years, photopolymerization initiators are often used as the polymerization initiator, and are generally used in combination of sensitizers and reducing agents.

For the sensitizers use may be made of camphor quinone, benzyl, diacetyl, benzyldimethylketal, benzyldiethylketal, benzyl di(2-methoxyethyl) ketal, 4,4'-dimethylbenzyl-dimethylketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluorothioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl) ketone, 4,4'-bisdiethylaminobenzophenone, and compounds containing an azido group, which may be used alone or in admixture.

For the reducing agents use may generally be made of tertiary amines. Preferable examples of the tertiary amine are N,N-dimethyl-p-toluidine, N,N-dimethylaminoethyl methacrylate, triethanolamine, methyl 4-dimethylaminobenzoate, ethyl 4-dimethylaminobenzoate, and isoamyl 4-dimethylaminobeonzoate. Other reducing agents inclusive of benzoyl peroxide, sulfinic acid sodium salt derivatives, and organic metal compounds may also be used.

For polymerization, the thus obtained photopolymerization type of bonding material may be irradiated with activated rays such as ultraviolet or visible rays. For the light source use may be made of various mercury lamps of ultra-high-pressure, high-pressure, moderate-pressure and low-pressure types, chemical lamps, carbon arc lamps, metal halide lamps, fluorescent lamps, tungsten lamps, xenon lamps, argon ion lasers, and so on.

For the chemical polymerization initiator use may be made of benzoyl peroxide and a tertiary amine; benzoyl peroxide and N-phenylglycine; benzoyl peroxide and p-toluenesulfinic acid sodium salt, benzoyl peroxide and benzenesulfinic acid sodium salt, benzoyl peroxide and p-toluensulfinic acid sodium salt or benzenesulfinic acid sodium salt and aromatic tertiary amine; potassium persulfate and an aromatic tertiary amine, sodium persulfate and an aromatic tertiary amine, and so on.

(g) The carbodiimide compound may be cyclohexylcarbodiimide, 1-ethyl-3-( 3-dimethylaminopropyl) carbodiimide, and 1-cyclohexyl-3-(2-morpholinoethyl) carbodiimide. In view of biological safety, however, 1-ethyl-3-(3-dimetylaminopropyl) carbodiimide is preferred, if the results of experimentation are taken into consideration. Preferably, this carbodiimide compound is used at a concentration of 0.1 to 10% by weight on the basis of the total weight of the bonding material. If the amount of the carbodiimide compound is less than this range, it will produce no effect, and if it is more than this range, the curing characteristics of the bonding material will get worse, resulting in a lowering of bonding strength.

To cure the bonding material from the tooth surface side so as to obtain an increased bonding strength, (thio)barbituric acid may be incorporated in the bonding material for reaction with the metal salt in the tooth surface-treating material.

In view of dental work, other additives such as UV absorbers, colorants and polymerization inhibitors may be used in slight amounts, if required, and fillers, solvents, and so on may be used as well.

Although not specifically limited, the tooth surface-treating material, primer and bonding material may be used in one-pack, two-pack, one-pack paste, two-pack paste, and powder-liquid forms. In terms of expediency, however, preference is given to a one-pack form. Also, the present invention may be applied to a potopolymerization type of (meth)acrylate-containing glass ionomer that has recently been commercially available in the market.

The present invention will now be explained, more illustratively but not exclusively, with reference to a number of examples.

EXAMPLE 1

A tooth surface-treating material was prepared, using 10 parts by weight of citric acid, 3 parts by weight of ferric chloride, and 87 parts by weight of distilled water.

A primer was prepared, using 65 parts by weight of distilled water, 35 parts by weight of 2-hydroxyethyl methacrylate, and 5 parts by weight of an acrylic acidmaleic acid copolymer.

A bonding material was prepared, using 70 parts by weight of 2-hydroxy methacrylate, 30 parts by weight of 2,2-bis[4-(2-hydroxy-3-methacryloxypropoxy) phenyl]propane, 0.5 parts by weight of camphor quinone, and 1.0 part by weight of dimethylaminoethyl methacrylate.

Using the thus prepared tooth surface-treating material, primer and bonding material, tests were made in terms of bonding strength and fitness. Set out in Table 1 are the composition and amount of each material and the results of the tests.

TABLE 1

|  | Tooth surface-treating materials | | Primers | |
| --- | --- | --- | --- | --- |
| Example 1 | Citric acid | 10.0 p. by w. | 2-hydroxyethyl methacrylate | 35.0 p. by w. |
|  | Ferric chloride | 3.0 | Acrylic acid-maleic acid copolymer | 5.0 |
|  | Distilled water | 87.0 | Distilled water | 65.0 |
| Example 2 | Polyacrylic acid | 10.0 p. by w. | 2-hydroxyethyl methacrylate | 50.0 p. by w. |
|  | Ferric chloride | 3.0 | Acrylic acid-maleic acid copolymer | 3.0 |
|  | Distilled water | 87.0 | Distilled water | 50.0 |
| Example 3 | Citric acid | 10.0 p. by w. | 2-hydroxyethyl methacrylate | 50.0 p. by w. |
|  | Cupric chloride | 3.0 | Polyacrylic acid | 5.0 |
|  | Distilled water | 87.0 | Distilled water | 50.0 |
| Example 4 | Oxalic acid | 3.0 p. by w. | 2-hydroxyethyl methacrylate | 35.0 p. by w. |
|  | Acetylacetone copper | 1.0 | Tartaric acid | 1.0 |
|  | Distilled water | 96.0 | Distilled water | 65.0 |
| Example 5 | Ethylenediamine-tetraacetic acid | 17.0 p. by w. | 2-hydroxyethyl methacrylate | 35.0 p. by w. |
|  | Ferric chloride | 3.0 | Polyacrylic acid | 3.0 |
|  |  |  | Distilled water | 65.0 |

TABLE 1-continued

Distilled water  80.0

| | Bonding materials (Photopolymerization type) | | Bonding Strength (kg/cm²) | | Fitness |
|---|---|---|---|---|---|
| | | | Enamel | Dentine | |
| Example 1 | 2-hydroxyethyl methacrylate | 70.0 p. by w. | 231 | 180 | a |
| | 2,2-bis[4-(2-hydroxy-3-methacryloxypropoxy) phenyl]propane | 30.0 | | | |
| | Camphorquinone | 0.5 | | | |
| | Dimethylaminoethyl methacrylate | 1.0 | | | |
| Example 2 | 2-hydroxyethyl methacrylate | 70.0 p. by w. | 205 | 215 | a |
| | 2,2-bis[4-(2-hydroxy-3-methacryloxypropoxy) phenyl]propane | 30.0 | | | |
| | 1-ethyl-3-(3-dimethylaminopropyl) carbodiimide | 1.0 | | | |
| | Camphorquinone | 0.5 | | | |
| | Dimethylaminoethyl methacrylate | 1.0 | | | |
| Example 3 | 2,2-bis(4-methacryloxypolyethoxyphenyl) propane | 100.0 p. by w. | 194 | 213 | a |
| | 1-ethyl-3-(3-dimethylaminopropyl) carbodiimide | 1.0 | | | |
| | Camphorquinone | 0.5 | | | |
| | Dimethylaminoethyl methacrylate | 1.0 | | | |
| Example 4 | 2,2-bis(4-methacryloxypolyethoxyphenyl) propane | 100.0 p. by w. | 228 | 207 | a |
| | 1-ethyl-3-(3-dimethylaminopropyl) carbodiimide | 1.0 | | | |
| | Camphorquinone | 0.5 | | | |
| | Dimethylaminoethyl methacrylate | 1.0 | | | |
| Example 5 | Triethyleneglycol dimethacrylate | 50.0 p. by w. | 222 | 182 | a |
| | 2,2-bis[4-(2-hydroxy-3-methacryloxypropoxy) phenyl]propane | 50.0 | | | |
| | Camphorquinone | 0.5 | | | |
| | Dimethylaminoethyl methacrylate | 1.0 | | | | p. by w. = part by weight

HOW TO MEASURE BONDING STRENGTH

1. The surfaces of the bovine fresh front teeth were polished by #600 water-resistant polishing paper in the presence of water, until the enamel and dentinal surfaces, five per each, are exposed.

2. The treating material was applied on each surface for 20 seconds, followed by water washing and drying.

3. A cellophane tape having a hole of 3.0 mm in diameter was applied over each of the thus treated surfaces. The primer was coated on a predetermined region of the surface, immediately followed by air drying. Then, the bonding material, when it was of the photopolymerization type, was coated on the tooth surface and then spread thinly thereon by use of air. Thereafter, it was irradiated with visible rays from a dental visible ray irradiator (GC Light, GC Corp.) for 20 seconds. The bonding material, when it was of the chemical polymerization type and the two or more pack type, was kneaded together, coated on the tooth surface, and spread thinly over it by use of air.

4. On a silicone rubber model having a hole of 5.0 mm in inner diameter and a thickness of 2.0 mm, a photopolymerization type of composite resin (Product name: Graft LCII, GC Corp.) was built up on the surface treated, and then irradiated with light from GC Light for 40 seconds for curing.

5. The test piece was immersed in water of 37° C. for 1 day. Following this, while a tensile acrylic rod was attached to the upper portion of the test piece, tensile testing was done at a cross head speed of 1.0 mm per minute with the use of an autograph (made by Shimadzu Corporation). Five measurements per enamel and dentine, respectively, were averaged to find bonding strength.

HOW TO OBSERVE FITNESS

1. A saucer type cavity was formed on the dental axis surface of a human extracted molar.

2. According to the aforesaid procedure of measuring bonding strength, the tooth surface-treating material, primer and bonding material were applied on the entire surface of the tooth, and the photopolymerization type of composite resin was filled and cured in the cavity.

3. After curing, the sample was stored in water of 37° C. for 24 hours. Following this, the middle portion of the cavity was sectioned vertically to the dental axis, and the section was smoothened with emery paper No. 1000 in the presence of water.

4. After the section was lightly etched by an aqueous solution of phosphoric acid, a precise replica of that section was made and then observed by SEM fractography for the estimation of fitness of the resin and the dentine.

5. The estimation of fitness was made by Sasazaki's method for estimating a resin-to-dentine gap ("The Japanese Journal of Conservative Dentistry", Vol. 28, No. 2, pp.

452–478, 1985) and according to the following five scores:
a: Good fitness with no gap
b: Very slight gap
c: less than 5 μm gap
d: 5–10 μm gap
e: more than 10 μm gap

EXAMPLES 2~13

As in Example 1, tooth surface-treating materials, primers and bonding materials were prepared for estimation. The compositions and amounts of the materials are shown in Tables 2 & 3. Again, similar tests were done as in Example 1.

TABLE 2

|  | Tooth surface-treating materials |  | Primers |  |
|---|---|---|---|---|
| Example 6 | Citric acid | 10.0 p. by w. | 2-hydroxyethyl methacrylate | 35.0 p. by w. |
|  | Ferric chloride | 0.1 | Polyacrylic acid | 3.0 |
|  | Distilled water | 90.0 | Distilled water | 65.0 |
| Example 7 | Polyacrylic acid | 48.0 p. by w. | 2-hydroxyethyl methacrylate | 35.0 p. by w. |
|  | Ferric chloride | 3.0 | Acrylic acid-maleic acid copolymer | 3.0 |
|  | Distilled water | 49.0 | Distilled water | 65.0 |
| Example 8 | Citric acid | 5.0 p. by w. | 2-hydroxyethyl methacrylate | 50.0 p. by w. |
|  | Cupric chloride | 0.001 | Acrylic acid-maleic acid copolymer | 25.0 |
|  | Distilled water | 95.0 | Distilled water | 25.0 |
| Example 9 | Maleic acid | 1.0 p. by w. | 2-hydroxyethyl methacrylate | 1.0 p. by w. |
|  | Acetylacetone copper | 1.0 | Polyacrylic acid | 3.0 |
|  | Distilled water | 98.0 | Distilled water | 96.0 |
| Example 10 | Ethylenediamine-tetraacetic acid | 17.0 p. by w. | 2-hydroxyethyl methacrylate | 90.0 p. by w. |
|  |  | 3.0 | Acrylic acid-maleic acid | 0.2 |
|  |  |  | Tartaric acid | 0.3 |
|  | Distilled water | 80.0 | Distilled water | 10.0 |

|  | Bonding materials (Photopolymerization type) |  | Bonding Strength (kg/cm$^2$) | | Fitness |
|---|---|---|---|---|---|
|  |  |  | Enamel | Dentine |  |
| Example 6 | 2-hydroxyethyl methacrylate | 70.0 p. by w. | 224 | 178 | a |
|  | 2,2-bis 4-(2-hydroxy-3-metha-cryloxypropoxy) phenyl propane | 30.0 |  |  |  |
|  | Camphorquinone | 0.5 |  |  |  |
|  | Dimethylaminoethyl methacrylate | 1.0 |  |  |  |
| Example 7 | 2-hydroxyethyl methacrylate | 70.0 p. by w. | 208 | 234 | a |
|  | 2,2-bis 4-(2-hydroxy-3-metha-cryloxypropoxy) phenyl propane | 30.0 |  |  |  |
|  | 1-ethyl-3-(3-dimethylamino-propyl) carbodiimide | 1.0 |  |  |  |
|  | Camphorquinone | 0.5 |  |  |  |
|  | Dimethylaminoethyl methacrylate | 1.0 |  |  |  |
| Example 8 | 2,2-bis(4-methacryloxypoly-ethoxyphenyl) propane | 100.0 p. by w. | 211 | 251 | a |
|  | 1-ethyl-3-(3-dimethylamino-propyl) carbodiimide | 0.2 |  |  |  |
|  | Camphorquinone | 0.5 |  |  |  |
|  | Dimethylaminoethyl methacrylate | 1.0 |  |  |  |
| Example 9 | 2,2-bis(4-methacryloxypoly-ethoxyphenyl) propane | 100.0 p. by w. | 217 | 229 | a |
|  | 1-ethyl-3-(3-dimethylamino-propyl) carbodiimide | 10.0 |  |  |  |
|  | Camphorquinone | 0.5 |  |  |  |
|  | Dimethylaminoethyl methacrylate | 1.0 |  |  |  |
| Example 10 | Triethyleneglycol dimethacrylate | 50.0 p. by w. | 235 | 218 | a |
|  | 2,2-bis 4-(2-hydroxy-3-metha-cryloxypropoxy) phenyl propane | 50.0 |  |  |  |
|  | 1-ethyl-3-(3-dimethylamino-propyl) carbodiimide | 1.0 |  |  |  |
|  | Camphorquinone | 0.5 |  |  |  |
|  | Dimethylaminoethyl methacrylate | 1.0 |  |  |  | p. by w. = part by weight

TABLE 3

| | Tooth surface-treating materials | | Primers | |
|---|---|---|---|---|
| Example 11 | Citric acid<br>Cupric chloride<br>Distilled water | 10.0 p. by w.<br>3.0<br>87.0 | 2-hydroxyethyl methacrylate<br>Acrylic acid-maleic acid copolymer<br>Distilled water | 35.0 p. by w.<br>3.0<br><br>65.0 |
| Example 12 | Acrylic acid-maleic acid copolymer<br>Ferric chloride<br>Distilled water | 10.0 p. by w.<br><br>48.0<br>42.0 | 2-hydroxyethyl methacrylate<br>Acrylic acid-maleic acid copolymer<br>Tartaric acid<br>Distilled water | 10.0 p. by w.<br>3.0<br><br>1.0<br>90.0 |
| Example 13 | Citric acid<br>Acetylacetone copper<br>Distilled water | 10.0 p. by w.<br>3.0<br><br>87.0 | 2-hydroxyethyl methacrylate<br>Polyacrylic acid<br>Distilled water | 35.0 p. by w.<br>3.0<br>65.0 |

| | Bonding materials<br>(Chemical polymerization type) | | Bonding Strength ($kg/cm^2$) | | Fitness |
|---|---|---|---|---|---|
| | | | Enamel | Dentine | |
| Example 11 | (Liquid A)<br>2-hydroxyethyl methacrylate<br>2,2-bis[4-(2-hydroxy-3-methacryloxypropoxy) phenyl]propane<br>1-ethyl-3-(3-dimethylaminopropyl) carbodiimide<br>N,N-dihydroxyethylparatoluidine<br>(Liquid B)<br>2-hydroxyethyl methacrylate<br>2,2-bis[4-(2-hydroxy-3-methacryloxypropoxy) phenyl]propane<br>Benzoyl peroxide | <br>70.0 p. by w.<br>30.0<br><br>2.0<br><br>1.0<br><br>70.0 p. by w.<br>30.0<br><br>1.0 | 255 | 218 | a |
| Example 12 | (Liquid A)<br>Ethanol<br>N,N-dihydroxyethylparatoluidine<br>p-toluenesulfinic acid salt<br>1-ethyl-3-(3-dimethylaminopropyl) carbodiimide<br>(Liquid B)<br>2-hydroxyethyl methacrylate<br>2,2-bis[4-(2-hydroxy-3-methacryloxypropoxy) phenyl]propane<br>Benzoyl peroxide | <br>100.0 p. by w.<br>1.0<br>1.0<br>3.0<br><br><br>70.0 p. by w.<br>30.0<br><br>1.0 | 214 | 223 | a |
| Example 13 | (Liquid A)<br>Ethanol<br>1-ethyl-3-(3-dimethylaminopropyl) carbodiimide<br>N-phenylglycine<br>(Liquid B)<br>2-hydroxyethyl methacrylate<br>Benzoyl peroxide | <br>100.0 p. by w.<br>2.0<br><br>1.0<br><br>100.0 p. by w.<br>1.0 | 248 | 240 | a | p. by w. = part by weight

COMPARATIVE EXAMPLES 1~14

Tooth surface-treating materials, primers and bonding materials were prepared for comparison with formulations free from the organic acid (a), iron or copper salt (b) and hydrophilic methacrylate (d) that are all the essential components of the present invention and in amounts departing from the ranges defined in the present dislcosure. The compositions and amounts of the materials are shown in Tables 4–6. Again, similar tests were done as in Example 1.

TABLE 4

| | Tooth surface-treating materials | | Primers | |
|---|---|---|---|---|
| Comparative Example 1 | Ferric chloride<br>Distilled water | 3.0 p. by w.<br>97.0 | 2-hydroxyethyl methacrylate<br>Acrylic acid-maleic acid copolymer<br>Distilled water | 35.0 p. by w.<br>3.0<br>65.0 |
| Comparative Example 2 | Citric acid<br>Distilled water | 10.0 p. by w.<br>90.0 | 2-hydroxyethyl methacrylate<br>Acrylic acid-maleic acid copolymer<br>Distilled water | 35.0 p. by w.<br>3.0<br>65.0 |
| Comparative Example 3 | Ferric chloride<br>Distilled water | 3.0 p. by w.<br>97.0 | 2-hydroxyethyl methacrylate<br>Acrylic acid-maleic acid copolymer<br>Distilled water | 35.0 p. by w.<br>3.0<br>65.0 |
| Comparative Example 4 | Citric acid<br>Distilled water | 10.0 p. by w.<br>90.0 | 2-hydroxyethyl methacrylate<br>Acrylic acid-maleic acid copolymer<br>Distilled water | 35.0 p. by w.<br>3.0<br>65.0 |

| | Bonding materials | | Bonding Strength (kg/cm$^2$) | | Fitness |
|---|---|---|---|---|---|
| | | | Enamel | Dentine | |
| Comparative Example 1 | 2-hydroxyethyl methacrylate<br>2,2-bis[4-(2-hydroxy-3-methacryloxypropoxy) phenyl]propane<br>Camphorquinone<br>Dimethylaminoethyl methacrylate<br>(Chemical polymerization type)<br>(Liquid A) | 70.0 p. by w.<br>30.0<br><br>0.5<br>1.0 | 45 | 30 | d |
| Comparative Example 2 | Ethanol<br>N,N-dihydroxyethylparatoluidine<br>p-toluenesulfinic acid sodium salt<br>(Liquid B)<br><br>2-hydroxyethyl methacrylate<br>2,2-bis[4-(2-hydroxy-3-methacryloxypropoxy) phenyl]propane<br>Benzoyl peroxide<br>(Photopolymerization type) | 100.0 p. by w.<br>1.0<br>1.0<br><br><br>70.0 p. by w.<br>30.0<br><br>1.0 | 144 | 68 | b |
| Comparative Example 3 | 2,2-bis(4-methacryloxypolyethoxyphenyl) propane<br>1-ethyl-3-(3-dimethylaminopropyl) carbodiimide<br>Camphorquinone<br>Dimethylaminoethyl methacrylate<br>(Photopolymerization type) | 100.0 p. by w.<br><br>1.0<br><br>0.5<br>1.0 | 30 | 24 | d |
| Comparative Example 4 | 2,2-bis (4-methacryloxypolyethoxyphenyl) propane<br>1-ethyl-3-(3-dimethylaminopropyl) carbodiimide<br>Camphorquinone<br>Dimethylaminoethyl methacrylate | 100.0 p. by w.<br><br>1.0<br><br>0.5<br>1.0 | 137 | 35 | c | p. by w. = part by weight

TABLE 5

| | Tooth surface-treating materials | | Primers | |
|---|---|---|---|---|
| Comparative | Citric acid<br>Ferric chloride<br>Distilled water | 10.0 p. by w.<br>3.0<br>87.0 | 2-hydroxyethyl methacrylate<br>Distilled water | 35.0 p. by w.<br>65.0 |

TABLE 5-continued

| Example | | | | |
|---|---|---|---|---|
| Comparative Example 5 | Citric acid<br>Ferric chloride<br>Distilled water | 10.0 p. by w.<br>3.0<br>87.0 | Acrylic acid-maleic acid copolymer<br>Distilled water | 3.0 p. by w.<br>97.0 |
| Comparative Example 6 | Citric acid<br>Ferric chloride<br>Distilled water | 10.0 p. by w.<br>3.0<br>87.0 | 2-hydroxyethyl methacrylate<br>Distilled water | 35.0 p. by w.<br>65.0 |
| Comparative Example 7 | Citric acid<br>Ferric chloride<br>Distilled water | 10.0 p. by w.<br>3.0<br>87.0 | Acrylic acid-maleic acid copolymer<br>Distilled water | 3.0 p. by w.<br>97.0 |
| Comparative Example 8 | Citric acid<br>Ferric chloride<br>Distilled water | 55.0 p. by w.<br>3.0<br>42.0 | 2-hydroxyethyl methacrylate<br>Acrylic acid-maleic acid copolymer<br>Distilled water | 35.0 p. by w.<br>3.0<br>65.0 |
| Comparative Example 9 | Oxalic acid<br>Cupric chloride<br>Distilled water | 15.0 p. by w.<br>55.0<br>30.0 | 2-hydroxyethyl methacrylate<br>Acrylic acid-maleic acid copolymer<br>Distilled water | 35.0 p. by w.<br>3.0<br>65.0 |
| Comparative Example 10 | | | | |

| | Bonding materials | | Bonding Strength (kg/cm$^2$) | | Fitness |
|---|---|---|---|---|---|
| | | | Enamel | Dentine | |
| Comparative Example 5 | (Photopolymerization type)<br>2-hydroxyethyl methacrylate<br>2,2-bis[4-(2-hydroxy-3-methacryloxypropoxy) phenyl]propane<br>Camphorquinone<br>Dimethylaminoethyl methacrylate | 70.0 p. by w.<br>30.0<br><br>0.5<br>1.0 | 188 | 44 | b |
| Comparative Example 6 | 2-hydroxyethyl methacrylate<br>2,2-bis[4-(2-hydroxy-3-methacryloxypropoxy) phenyl]propane<br>Camphorquinone<br>Dimethylaminoethyl methacrylate | 70.0 p. by w.<br>30.0<br><br>0.5<br>1.0 | 190 | 70 | b |
| Comparative Example 7 | (Photopolymerization type)<br>2-hydroxyethyl methacrylate<br>2,2-bis[4-(2-hydroxy-3-methacryloxypropoxy) phenyl]propane<br>1-ethyl-3-(3-dimethylaminopropyl) carbodiimide<br>Camphorquinone<br>Dimethylaminoethyl methacrylate | 70.0 p. by w.<br>30.0<br><br>1.0<br><br>0.5<br>1.0 | 180 | 59 | b |
| Comparative Example 8 | 2-hydroxyethyl methacrylate<br>2,2-bis[4-(2-hydroxy-3-methacryloxypropoxy) phenyl]propane<br>1-ethyl-3-(3-dimethylaminopropyl) carbodiimide<br>Camphorquinone<br>Dimethylaminoethyl methacrylate | 70.0 p. by w.<br>30.0<br><br>1.0<br><br>0.5<br>1.0 | 210 | 66 | b |
| Comparative Example 9 | 2,2-bis(4-methacryloxypolyethoxyphenyl) propane<br>1-ethyl-3-(3-dimethylaminopropyl) carbodiimide<br>Camphorquinone<br>Dimethylaminoethyl methacrylate | 100.0 p. by w.<br><br>1.0<br><br>0.5<br>1.0 | 173 | 24 | c |
| Comparative Example 10 | 2,2-bis(4-methacryloxypolyethoxyphenyl) propane<br>1-ethyl-3-(3-dimethylaminopropyl) carbodiimide<br>Camphorquinone<br>Dimethylaminoethyl methacrylate | 100.0 p. by w.<br><br>1.0<br><br>0.5<br>1.0 | 155 | 18 | c |

TABLE 5-continued p. by w. = part by weight

TABLE 6

| | Tooth surface-treating materials | | Primers | |
|---|---|---|---|---|
| Comparative Example 11 | Ethylenediamine-tetraacetic acid<br>Cubic chloride<br>Distilled water | 17.0 p. by w.<br>3.0<br>80.0 | 2-hydroxyethyl methacrylate<br>Acrylic acid-maleic acid copolymer<br>Distilled water | 35.0 p. by w.<br>35.0<br>30.0 |
| Comparative Example 12 | Citric acid<br>Cupric chloride<br>Distilled water | 10.0 p. by w.<br>3.0<br>87.0 | 2-hydroxyethyl methacrylate<br>Acrylic acid-maleic acid copolymer<br>Distilled water | 35.0 p. by w.<br>0.05<br>65.0 |
| Comparative Example 13 | Oxalic acid<br>Cupric chloride<br>Distilled water | 15.0 p. by w.<br>1.0<br>84.0 | 2-hydroxyethyl methacrylate<br>Acrylic acid-maleic acid copolymer<br>Distilled water | 35.0 p. by w.<br>3.0<br>65.0 |
| Comparative Example 14 | Citric acid<br>Cupric chloride<br>Distilled water | 15.0 p. by w.<br>1.0<br>84.0 | 2-hydroxyethyl methacrylate<br>Acrylic acid-maleic acid copolymer<br>Distilled water | 35.0 p. by w.<br>3.0<br>65.0 |

| | Bonding materials (Photoporymerization type) | | Bonding Strength (kg/cm$^2$) | | Fitness |
|---|---|---|---|---|---|
| | | | Enamel | Dentine | |
| Comparative Example 11 | Triethyleneglycol dimethacrylate<br>2,2-bis[4-(2-hydroxy-3-methacryloxypropoxy) phenyl]propane<br>1-ethyl-3-(3-dimethylaminopropyl) carbodiimide<br>Camphorquinone<br>Dimethylaminoethyl methacrylate | 50.0 p. by w.<br>50.0<br>1.0<br>0.5<br>1.0 | 61 | 21 | d |
| Comparative Example 12 | (Liquid A)<br>2-hydroxyethyl methacrylate<br>2,2-bis[4-(2-hydroxy-3-methacryloxypropoxy) phenyl]propane<br>1-ethyl-3-(3-dimethylaminopropyl) carbodiimide<br>N,N-dihydroxyethylparatoluidine<br>(Liquid B)<br>2-hydroxyethyl methacrylate<br>2,2-bis[4-(2-hydroxy-3-methacryloxypropoxy) phenyl]propane<br>Benzoyl peroxide | 40.0 p. by w.<br>35.0<br>1.0<br>1.0<br>70.0 p. by w.<br>30.0<br>1.0 | 153 | 61 | b |
| Comparative Example 13 | 2,2-bis(4-methacryloxypolyethoxyphenyl) propane<br>1-ethyl-3-(3-dimethylaminopropyl) carbodiimide<br>Camphorquinone<br>Dimethylaminoethyl methacrylate | 100.0 p. by w.<br>0.05<br>0.5<br>1.0 | 145 | 58 | c |
| Comparative Example 14 | 2,2-bis(4-methacryloxypolyethoxyphenyl) propane<br>1-ethyl-3-(3-dimethylaminopropyl) carbodiimide<br>Camphorquinone<br>Dimethylaminoethyl methacrylate | 100.0 p. by w.<br>15.0<br>0.5<br>1.0 | 105 | 18 | c | p. by w. = part by weight

By experimentation, the dental bonding method according to the present invention is confirmed to achieve strong bonding strength to the dentine. Observation of the fitness of the materials to human extracted teeth also indicates that the resin is well bonded to the dentine and that gaps, the leading cause of secondary caries, are not found at all.

What is claimed is:

1. A dental bonding method comprising the steps of treating enamel and dentine with a tooth surface-treating material containing (a) organic acid, (b) iron or copper salt, and (c) water, followed by water washing and drying; applying on the thus treated surface a primer containing (a) organic acid, (c) water, and (d) hydrophilic methacrylate, followed by drying; and applying on the thus coated surface a dental bonding material containing (e) methacrylate or acrylate having at least one unsaturated double bond, and (f) polymerization initiator for surface curing.

2. A dental bonding method comprising the steps of treating enamel and dentine with a tooth surface-treating material containing (a) organic acid, (b) iron or copper salt, and (c) water, followed by water washing and drying; applying on the thus treated surface a primer containing (a) organic acid, (c) water, and (d) hydrophilic methacrylate, followed by drying; and applying on the thus coated surface a dental bonding material containing (e) methacrylate or acrylate having at least one unsaturated double bond, (f) polymerization initiator, and (g) carbodiimide compound for surface curing.

3. A dental bonding method as claimed in claim 1 or 2, wherein the organic acid (a) is selected from the group consisting of citric acid, succinic acid, oxalic acid, fumaric acid, tartaric acid, malic acid, maleic acid, ethylenediaminetetraacetic acid, polyacrylic acid, acrylic acid-maleic acid copolymer, or copolymer of acrylic acid with organic acid having unsaturated double bond.

4. A dental bonding method as claimed in claim 1 or 2, wherein the concentration of the organic acid (a) in the tooth surface-treating material is 1 to 50% by weight on the basis of the total weight of the tooth surface-treating material.

5. A dental bonding method as claimed in claim 1 or 2, wherein the iron or copper salt (b) is ferric chloride, cupric chloride or acetylacetone copper.

6. A dental bonding method as claimed in claim 1 or 2, wherein the concentration of the iron or copper salt (b) is 0.0005 to 50% by weight on the basis of the total weight of the tooth surface-treating material.

7. A dental bonding method as claimed in claim 1 or 2, wherein the hydrophilic methacrylate (d) is 2-hydroxethyl methacrylate.

8. A dental bonding method as claimed in claim 1 or 2, wherein the concentration of the hydrophilic methacrylate (d) is 1 to 90% by weight on the basis of the total weight of the primer.

9. A dental bonding method as claimed in claim 1 or 2, wherein the concentration of the organic acid (a) is 0.1 to 30% by weight on the basis of the total weight of the primer.

10. A dental bonding method as claimed in claim 2, wherein the carbodiimide compound (g) is 1-ethyl-3-(3-dimethylaminopropyl)carbodiimide.

11. A dental bonding method as claimed in claim 2, wherein the concentration of the carbodiimide compound (g) is 0.1 to 10% by weight on the basis of the total weight of the dental bonding material.

* * * * *